United States Patent
Chavan

(10) Patent No.: US 12,420,005 B2
(45) Date of Patent: *Sep. 23, 2025

(54) URINARY DRAINAGE SYSTEM WITH AIR PRESSURE APPARATUS

(71) Applicant: C. R. Bard, Inc., Franklin Lakes, NJ (US)

(72) Inventor: Varad Chavan, Kolhapur (IN)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/674,694

(22) Filed: May 24, 2024

(65) Prior Publication Data

US 2024/0307604 A1    Sep. 19, 2024

Related U.S. Application Data

(63) Continuation of application No. 17/561,504, filed on Dec. 23, 2021, now Pat. No. 11,992,599.

(60) Provisional application No. 63/135,458, filed on Jan. 8, 2021.

(51) Int. Cl.
*A61M 1/00* (2006.01)
*A61M 27/00* (2006.01)

(52) U.S. Cl.
CPC .............. *A61M 1/86* (2021.05); *A61M 1/70* (2021.05); *A61M 27/00* (2013.01); *A61M 2210/1085* (2013.01)

(58) Field of Classification Search
None
See application file for complete search history.

(56) References Cited

U.S. PATENT DOCUMENTS

| | | |
|---|---|---|
| 3,114,916 A | 12/1963 | Hadley |
| 3,583,401 A | 6/1971 | Vailiancourt et al. |
| 3,598,124 A | 8/1971 | Andersen et al. |
| 3,661,143 A | 5/1972 | Henkin |
| 3,861,394 A | 1/1975 | Villari |

(Continued)

FOREIGN PATENT DOCUMENTS

| | | |
|---|---|---|
| CN | 106955208 A | 7/2017 |
| CN | 116650740 A | 8/2023 |

(Continued)

OTHER PUBLICATIONS

PCT/US2020/066707 filed Dec. 22, 2020 International Search Report and Written Opinion dated Apr. 15, 2021.

(Continued)

*Primary Examiner* — Catharine L Anderson
*Assistant Examiner* — Katherine-Ph Minh Pham
(74) *Attorney, Agent, or Firm* — Rutan & Tucker LLP

(57) ABSTRACT

A urinary drainage system can include an air pressure apparatus with a connector having an elongate connector body. The connector includes a lumen having a larger proximal lumen diameter and a smaller distal lumen diameter. The system includes an air intake adapter having an elongate adapter body, including a proximal end having a proximal opening configured to be coupled to the distal end of the connector. The adapter can include an air intake port in fluid communication with the adapter lumen, the adapter lumen having a larger proximal lumen diameter and a smaller distal lumen diameter.

16 Claims, 6 Drawing Sheets

(56) References Cited

U.S. PATENT DOCUMENTS

| | | |
|---|---|---|
| 3,901,235 A | 8/1975 | Patel et al. |
| 3,955,574 A | 5/1976 | Rubinstein |
| 4,084,593 A | 4/1978 | Jarund |
| 4,265,243 A | 5/1981 | Taylor |
| 4,305,403 A | 12/1981 | Dunn |
| 4,315,506 A | 2/1982 | Kayser et al. |
| 4,360,933 A | 11/1982 | Kimura et al. |
| 4,465,485 A | 8/1984 | Kashmer et al. |
| 4,490,144 A | 12/1984 | Steigerwald |
| 4,531,939 A | 7/1985 | Izumi |
| 4,556,997 A | 12/1985 | Takamiya et al. |
| 4,631,061 A | 12/1986 | Martin |
| 4,654,029 A | 3/1987 | D'Antonio |
| 4,747,166 A | 5/1988 | Kuntz |
| 4,810,242 A | 3/1989 | Sundblom et al. |
| 4,819,684 A | 4/1989 | Zaugg et al. |
| 4,872,579 A | 10/1989 | Palmer |
| 4,880,411 A | 11/1989 | Fangrow, Jr. et al. |
| 4,990,137 A | 2/1991 | Graham |
| 5,002,528 A | 3/1991 | Palestrant |
| 5,071,411 A | 12/1991 | Hillstead |
| 5,186,431 A | 2/1993 | Tamari |
| 5,242,404 A | 9/1993 | Conley et al. |
| 5,318,550 A | 6/1994 | Cermak et al. |
| 5,359,233 A | 10/1994 | Mumper et al. |
| 5,405,319 A | 4/1995 | Abell et al. |
| RE35,707 E | 12/1997 | Takamiya et al. |
| 5,738,656 A | 4/1998 | Wagner |
| 5,813,842 A | 9/1998 | Tamari |
| 5,894,608 A | 4/1999 | Birbara |
| 6,007,521 A | 12/1999 | Bidwell et al. |
| 6,106,506 A | 8/2000 | Abell et al. |
| 6,183,454 B1 | 2/2001 | Levine et al. |
| 8,266,741 B2 | 9/2012 | Penninger et al. |
| 8,337,475 B2 | 12/2012 | Christensen et al. |
| 8,475,419 B2 | 7/2013 | Eckermann |
| 8,512,301 B2 | 8/2013 | Ma |
| 9,814,866 B1 | 11/2017 | Goswami |
| 10,391,275 B2 | 8/2019 | Burnett et al. |
| 10,426,919 B2 | 10/2019 | Erbey, II et al. |
| 10,506,965 B2 | 12/2019 | Cooper et al. |
| 10,737,057 B1 | 8/2020 | Mikhail et al. |
| 10,772,998 B2 | 9/2020 | Luxon et al. |
| 2002/0000253 A1 | 1/2002 | Fillmore et al. |
| 2002/0161317 A1 | 10/2002 | Risk et al. |
| 2003/0078638 A1 | 4/2003 | Voorhees et al. |
| 2004/0176746 A1 | 9/2004 | Forral |
| 2004/0230181 A1 | 11/2004 | Cawood |
| 2004/0236292 A1 | 11/2004 | Tazoe et al. |
| 2004/0254547 A1 | 12/2004 | Okabe et al. |
| 2005/0197647 A1 | 9/2005 | Dolliver et al. |
| 2005/0209585 A1 | 9/2005 | Nord et al. |
| 2005/0245898 A1 | 11/2005 | Wright et al. |
| 2005/0256460 A1 | 11/2005 | Rome et al. |
| 2005/0261619 A1 | 11/2005 | Gay |
| 2006/0015190 A1 | 1/2006 | Robertson |
| 2006/0079854 A1 | 4/2006 | Kay et al. |
| 2006/0155260 A1 | 7/2006 | Blott et al. |
| 2006/0235353 A1 | 10/2006 | Gelfand et al. |
| 2006/0270971 A1 | 11/2006 | Gelfand et al. |
| 2006/0271019 A1 | 11/2006 | Stoller et al. |
| 2007/0005002 A1 | 1/2007 | Millman et al. |
| 2007/0078444 A1 | 4/2007 | Larsson |
| 2007/0142729 A1 | 6/2007 | Pfeiffer et al. |
| 2007/0272311 A1 | 11/2007 | Trocki et al. |
| 2008/0051708 A1 | 2/2008 | Kumar et al. |
| 2008/0156092 A1 | 7/2008 | Boiarski |
| 2008/0281254 A1 | 11/2008 | Humayun et al. |
| 2009/0157016 A1 | 6/2009 | Adahan |
| 2009/0157040 A1 | 6/2009 | Jacobson et al. |
| 2009/0326483 A1 | 12/2009 | Green |
| 2010/0106116 A1 | 4/2010 | Simmons et al. |
| 2010/0130949 A1 | 5/2010 | Garcia |
| 2010/0280435 A1 | 11/2010 | Raney et al. |
| 2011/0060300 A1 | 3/2011 | Weig et al. |
| 2012/0036638 A1 | 2/2012 | Penninger et al. |
| 2012/0323144 A1 | 12/2012 | Coston et al. |
| 2013/0218106 A1 | 8/2013 | Coston et al. |
| 2014/0053841 A1* | 2/2014 | Ratner ............ A61M 16/0057 |
| | | 128/204.25 |
| 2014/0200558 A1 | 7/2014 | McDaniel |
| 2015/0126975 A1 | 5/2015 | Wuthier |
| 2015/0290448 A1 | 10/2015 | Pavlik |
| 2016/0135982 A1 | 5/2016 | Garcia |
| 2016/0183819 A1 | 6/2016 | Burnett et al. |
| 2016/0310711 A1 | 10/2016 | Luxon et al. |
| 2017/0014617 A1 | 1/2017 | Huici |
| 2017/0072125 A1 | 3/2017 | Wallenås et al. |
| 2017/0136209 A1 | 5/2017 | Burnett et al. |
| 2017/0143566 A1 | 5/2017 | Elku et al. |
| 2017/0241978 A1 | 8/2017 | Duval |
| 2017/0312114 A1 | 11/2017 | Glithero |
| 2018/0015251 A1 | 1/2018 | Lampotang et al. |
| 2018/0071441 A1 | 3/2018 | Croteau et al. |
| 2018/0104391 A1 | 4/2018 | Luxon et al. |
| 2018/0110456 A1 | 4/2018 | Cooper et al. |
| 2018/0125697 A1 | 5/2018 | Ferrera |
| 2018/0177458 A1 | 6/2018 | Burnett et al. |
| 2018/0235523 A1 | 8/2018 | Sauder |
| 2018/0245699 A1 | 8/2018 | Lee |
| 2018/0360424 A1 | 12/2018 | Yurek et al. |
| 2019/0009021 A1 | 1/2019 | Nelson et al. |
| 2019/0009023 A1 | 1/2019 | Diperna et al. |
| 2019/0030264 A1* | 1/2019 | Herskovic ............ A61M 39/10 |
| 2019/0038451 A1 | 2/2019 | Harvie |
| 2019/0046102 A1 | 2/2019 | Kushnir et al. |
| 2019/0126006 A1 | 5/2019 | Rehm et al. |
| 2019/0143008 A1 | 5/2019 | Brundage et al. |
| 2019/0143094 A1 | 5/2019 | DeMeritt |
| 2019/0151610 A1 | 5/2019 | Fletter |
| 2019/0343445 A1* | 11/2019 | Burnett .................. A61B 5/207 |
| 2020/0000979 A1 | 1/2020 | Myers |
| 2020/0061281 A1 | 2/2020 | Desouza et al. |
| 2020/0315837 A1 | 10/2020 | Radl et al. |
| 2021/0077007 A1 | 3/2021 | Jouret et al. |
| 2022/0152345 A1 | 5/2022 | Simiele et al. |
| 2022/0160949 A1 | 5/2022 | Simiele et al. |
| 2022/0176031 A1 | 6/2022 | Cheng et al. |
| 2022/0193366 A1 | 6/2022 | Cheng et al. |
| 2022/0218890 A1 | 7/2022 | Chavan |
| 2022/0218973 A1 | 7/2022 | Chavan et al. |
| 2022/0218974 A1 | 7/2022 | Chavan et al. |
| 2022/0273213 A1 | 9/2022 | Sokolov et al. |
| 2022/0287689 A1 | 9/2022 | Johannes |
| 2022/0305189 A1 | 9/2022 | Chavan et al. |
| 2022/0330867 A1 | 10/2022 | Conley et al. |
| 2022/0362080 A1 | 11/2022 | McCorquodale et al. |
| 2022/0409421 A1 | 12/2022 | Hughett et al. |
| 2023/0013353 A1 | 1/2023 | Chavan et al. |
| 2023/0030637 A1 | 2/2023 | Gloeckner et al. |
| 2023/0054937 A1 | 2/2023 | Chancy et al. |
| 2023/0083906 A1 | 3/2023 | Jones et al. |
| 2023/0277199 A1 | 9/2023 | Duffy |
| 2023/0310837 A1 | 10/2023 | Gamsizlar et al. |
| 2024/0033404 A1 | 2/2024 | Ishikawa |
| 2024/0238500 A1 | 7/2024 | Simiele et al. |
| 2025/0009578 A1 | 1/2025 | Chancy et al. |
| 2025/0018147 A1 | 1/2025 | Rehm |
| 2025/0018149 A1 | 1/2025 | Cheng et al. |
| 2025/0025617 A1 | 1/2025 | Chavan et al. |
| 2025/0025620 A1 | 1/2025 | Cheng et al. |
| 2025/0040848 A1 | 2/2025 | Lai et al. |

FOREIGN PATENT DOCUMENTS

| | | |
|---|---|---|
| EP | 1872752 A1 | 1/2008 |
| EP | 2417955 A2 | 2/2012 |
| EP | 2730299 A1 | 5/2014 |
| WO | 2009026237 A1 | 2/2009 |
| WO | 2012016179 A1 | 2/2012 |
| WO | 2015019056 A1 | 2/2015 |
| WO | 2015105916 A1 | 7/2015 |
| WO | 2016012494 A1 | 1/2016 |
| WO | 2017177068 A1 | 10/2017 |

(56) References Cited

FOREIGN PATENT DOCUMENTS

| WO | 2018136306 A1 | 7/2018 |
|---|---|---|
| WO | 2018191193 A1 | 10/2018 |
| WO | 2019004854 A1 | 1/2019 |
| WO | 2020033752 A1 | 2/2020 |
| WO | 2021154427 A1 | 8/2021 |
| WO | 2022159333 A1 | 7/2022 |
| WO | 2022251425 A1 | 12/2022 |
| WO | 2023086394 A1 | 5/2023 |

OTHER PUBLICATIONS

PCT/US2022/012373 filed Jan. 13, 2022 International Search Report and Written Opinion dated Apr. 19, 2022.
PCT/US2022/049418 filed Nov. 9, 2022 International Search Report and Written Opinion dated Feb. 10, 2023.
U.S. Appl. No. 17/373,568, filed Jul. 12, 2021 Non-Final Office Action dated Nov. 9, 2023.
U.S. Appl. No. 17/373,568, filed Jul. 12, 2021 Notice of Allowance dated Apr. 26, 2024.
U.S. Appl. No. 17/526,994, filed Nov. 15, 2021 Advisory Action dated Jan. 19, 2024.
U.S. Appl. No. 17/526,994, filed Nov. 15, 2021 Final Office Action dated Oct. 24, 2023.
U.S. Appl. No. 17/526,994, filed Nov. 15, 2021 Non-Final Office Action dated Apr. 22, 2024.
U.S. Appl. No. 17/526,994, filed Nov. 15, 2021 Non-Final Office Action dated May 10, 2023.
U.S. Appl. No. 17/526,994, filed Nov. 15, 2021 Restriction Requirement dated Jan. 3, 2023.
U.S. Appl. No. 17/532,454, filed Nov. 22, 2021 Final Office Action dated Sep. 27, 2023.
U.S. Appl. No. 17/532,454, filed Nov. 22, 2021 Non-Final Office Action dated Mar. 22, 2023.
U.S. Appl. No. 17/532,454, filed Nov. 22, 2021 Notice of Allowance dated Dec. 8, 2023.
U.S. Appl. No. 17/542,060, filed Dec. 3, 2021 Non-Final Office Action dated Jun. 27, 2023.
U.S. Appl. No. 17/542,060, filed Dec. 3, 2021 Non-Final Office Action dated Nov. 28, 2023.
U.S. Appl. No. 17/542,060, filed Dec. 3, 2021 Notice of Allowance dated Jun. 3, 2024.
U.S. Appl. No. 17/556,942, filed Dec. 20, 2021 Advisory Action dated Sep. 1, 2023.
U.S. Appl. No. 17/556,942, filed Dec. 20, 2021 Final Office Action dated Apr. 4, 2024.
U.S. Appl. No. 17/556,942, filed Dec. 20, 2021 Final Office Action dated Jul. 12, 2023.
U.S. Appl. No. 17/556,942, filed Dec. 20, 2021 Non-Final Office Action dated Jan. 31, 2023.
U.S. Appl. No. 17/556,942, filed Dec. 20, 2021 Non-Final Office Action dated Nov. 3, 2023.
U.S. Appl. No. 17/561,458, filed Dec. 23, 2021 Final Office Action dated Sep. 12, 2023.
U.S. Appl. No. 17/561,458, filed Dec. 23, 2021 Non-Final Office Action dated Jun. 16, 2023.
U.S. Appl. No. 17/561,458, filed Dec. 23, 2021 Notice of Allowance dated Dec. 6, 2023.
U.S. Appl. No. 17/561,504, filed Dec. 23, 2021 Final Office Action dated Jul. 19, 2023.
U.S. Appl. No. 17/561,504, filed Dec. 23, 2021 Non-Final Office Action dated Mar. 14, 2023.
U.S. Appl. No. 17/561,504, filed Dec. 23, 2021 Non-Final Office Action dated Nov. 27, 2023.
U.S. Appl. No. 17/561,504, filed Dec. 23, 2021 Notice of Allowance dated Jan. 22, 2024.
U.S. Appl. No. 17/796,604, filed Jul. 29, 2022 Notice of Allowance dated May 1, 2024.
U.S. Appl. No. 17/863,898, filed Jul. 13, 2022 Advisory Action dated Jan. 30, 2024.
U.S. Appl. No. 17/863,898, filed Jul. 13, 2022 Final Office Action dated Nov. 22, 2023.
U.S. Appl. No. 17/863,898, filed Jul. 13, 2022 Non-Final Office Action dated Jul. 17, 2023.
U.S. Appl. No. 17/863,898, filed Jul. 13, 2022 Non-Final Office Action dated Mar. 11, 2024.
U.S. Appl. No. 17/902,705, filed Sep. 2, 2022 Advisory Action dated Oct. 19, 2023.
U.S. Appl. No. 17/902,705, filed Sep. 2, 2022 Final Office Action dated Aug. 17, 2023.
U.S. Appl. No. 17/902,705, filed Sep. 2, 2022 Final Office Action dated May 22, 2024.
U.S. Appl. No. 17/902,705, filed Sep. 2, 2022 Non-Final Office Action dated Dec. 7, 2023.
U.S. Appl. No. 17/902,705, filed Sep. 2, 2022 Non-Final Office Action dated May 24, 2023.
U.S. Appl. No. 17/526,994, filed Nov. 15, 2021 Final Office Action dated Nov. 19, 2024.
U.S. Appl. No. 17/556,942, filed Dec. 20, 2021 Notice of Allowance dated Jun. 26, 2024.
U.S. Appl. No. 17/571,254, filed Jan. 7, 2022 Restriction Requirement dated Oct. 4, 2024.
U.S. Appl. No. 17/863,898, filed Jul. 13, 2022 Advisory Action dated Oct. 28, 2024.
U.S. Appl. No. 17/863,898, filed Jul. 13, 2022 Final Office Action dated Aug. 22, 2024.
U.S. Appl. No. 17/863,898, filed Jul. 13, 2022 Non-Final Office Action dated Dec. 2, 2024.
U.S. Appl. No. 17/902,705, filed Sep. 2, 2022 Advisory Action dated Aug. 1, 2024.
U.S. Appl. No. 17/902,705, filed Sep. 2, 2022 Notice of Allowance dated Sep. 18, 2024.
U.S. Appl. No. 17/526,994, filed Nov. 15, 2021 Notice of Allowance dated Feb. 5, 2025.
U.S. Appl. No. 17/571,254, filed Jan. 7, 2022 Non-Final Office Action dated Feb. 13, 2025.
U.S. Appl. No. 18/274,157, filed Jul. 25, 2023 Final Office Action dated May 5, 2025.
U.S. Appl. No. 18/274,157, filed Jul. 25, 2023 Non-Final Office Action dated Jan. 17, 2025.

* cited by examiner

URINARY DRAINAGE SYSTEM WITH AIR PRESSURE APPARATUS

PRIORITY

This application is a continuation of U.S. patent application Ser. No. 17/561,504, filed Dec. 23, 2021, now U.S. Pat. No. 11,992,599, which claims the benefit of priority to U.S. Provisional Application No. 63/135,458, filed Jan. 8, 2021, each of which is incorporated by reference in its entirety into this application.

BACKGROUND

Urine transport from a patient to a urine collection bag may be facilitated by gravity. In some configurations, the collection bag and drainage tubing connecting to the patient must be sloped downward with the bag at a lower height than the patient's bladder. However due to normal patient movement over time, the drainage tubing may incur tubing loops that lead to a volume of urine that is retained within the tubing and does not reach the bag. The retained urine within the tubing can lead to inaccurate urine output measurements and increased pressure on the patients' bladder to expel the urine into the bag. The increased pressure can lead to injury if the pressure is not alleviated in a timely manner. Current methods to clear the retained urine within the tubing require clinicians to lift the tubing to push the fluid towards the bag. It would be beneficial to the patient and the clinician to have a system that ensures all urine from the bladder gets transported to the collection bag within additional steps. Disclosed herein is an apparatus, a system and method of use that address the foregoing.

SUMMARY

Disclosed herein is a urinary drainage system including an air pressure apparatus having a connector having an elongate connector body, including a proximal end having a proximal opening, a distal end including a distal opening and a connector lumen. The connector lumen includes a larger proximal lumen diameter and a smaller distal lumen diameter. The air pressure apparatus includes an air intake adapter having an elongate adapter body, including a proximal end having a proximal opening configured to be coupled to the distal end of the connector, a distal end having a distal opening, the adapter body having an adapter lumen and an air intake port. The air intake port is in fluid communication with the adapter lumen, the adapter lumen having a larger proximal lumen diameter and a smaller distal lumen diameter.

In some embodiments, the urinary drainage system includes a catheter in fluid communication with a fluid collecting bag.

In some embodiments, the catheter is coupled to the proximal end of the connector.

In some embodiments, the catheter is coupled to the proximal end of the connector by a first drainage tube.

In some embodiments, the fluid collecting bag is coupled to the distal end of the adapter.

In some embodiments, the fluid collecting bag is coupled to the distal end of the adapter by a second drainage tube.

In some embodiments, the connector lumen is in fluid communication with the adapter lumen when the distal end of the connector is coupled to the proximal end of the adapter.

In some embodiments, the proximal lumen diameter of the adapter is larger than the distal lumen diameter of the connector.

In some embodiments, the coupling of the adapter to the connector generates a luminal space within the adapter, the luminal space being in fluid communication with the air intake port.

In some embodiments, the air intake port is perpendicular to the distal end of the connector.

In some embodiments, a volume of positive pressurized air is received through the air intake port, creating a vortex of positive air pressure within the luminal space.

In some embodiments, the distal end of the connector includes external threads thereon and the proximal end of the adapter includes internal threads therein, the external threads and internal threads configured to couple the connector to the adapter.

In some embodiments, the connector includes one or more lateral ports perpendicular to the connector lumen, the one or more lateral ports being in fluid communication with the connector lumen and being configured to draw fluid.

In some embodiments, the proximal end of the connector includes a catheter attachment.

In some embodiments, the connector lumen is in fluid communication with the catheter or the first drainage tube.

In some embodiments, the proximal end of the connector is configured to slidably receive the catheter or the first drainage tube.

In some embodiments, the adapter lumen is in fluid communication with the second drainage tube.

In some embodiments, the distal end of the adapter is configured to slidably receive the second drainage tube.

In some embodiments, the connector and the adapter are disposable or reusable.

Also disclosed herein is a method for clearing a fluid column from a drainage tube including coupling an air pressure apparatus of a urinary drainage system to a catheter and to a fluid collecting bag, the air pressure apparatus maintaining fluid communication between the catheter and the fluid collecting bag, the air pressure apparatus having a connector including a connector lumen, the connector coupled to an adapter having an adapter lumen, an air intake port and a luminal space. The method further includes passing an acquired volume of fluid from the catheter to the fluid collecting bag, providing a volume of positive air pressure into the luminal space of the adapter, and clearing a first drainage tube of a residual volume of fluid.

In some embodiments, coupling the air pressure apparatus of the urinary drainage system to the catheter and to the fluid collecting bag includes a proximal end of the connector slidably receiving a first drainage tube coupled to the catheter and a distal end of the adapter slidably receiving a second drainage tube coupled to the fluid collecting bag.

In some embodiments, coupling the air pressure apparatus of the urinary drainage system to the catheter and to the fluid collecting bag includes the proximal end of the connector slidably receiving the catheter and the distal end of the adapter slidably receiving the second drainage tube.

In some embodiments, the connector lumen and the adapter lumen are in fluid communication with the catheter and the fluid collecting bag.

In some embodiments, passing the acquired volume of fluid includes passing by gravity flow.

In some embodiments, providing a volume of positive air pressure includes coupling an air hose connected to a motor to the air intake port of the adapter.

In some embodiments, providing a volume of positive air pressure includes providing a volume of positive air pressure through the air intake port.

In some embodiments, providing a volume of positive air pressure includes creating a vortex of positive air pressure around the distal end of the connector.

In some embodiments, clearing the first drainage tube of the residual volume of fluid includes using the vortex of positive air pressure to draw the volume of fluid into the connector lumen and push the entire volume of fluid out of a distal end of the adapter.

These and other features of the concepts provided herein will become more apparent to those of skill in the art in view of the accompanying drawings and following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
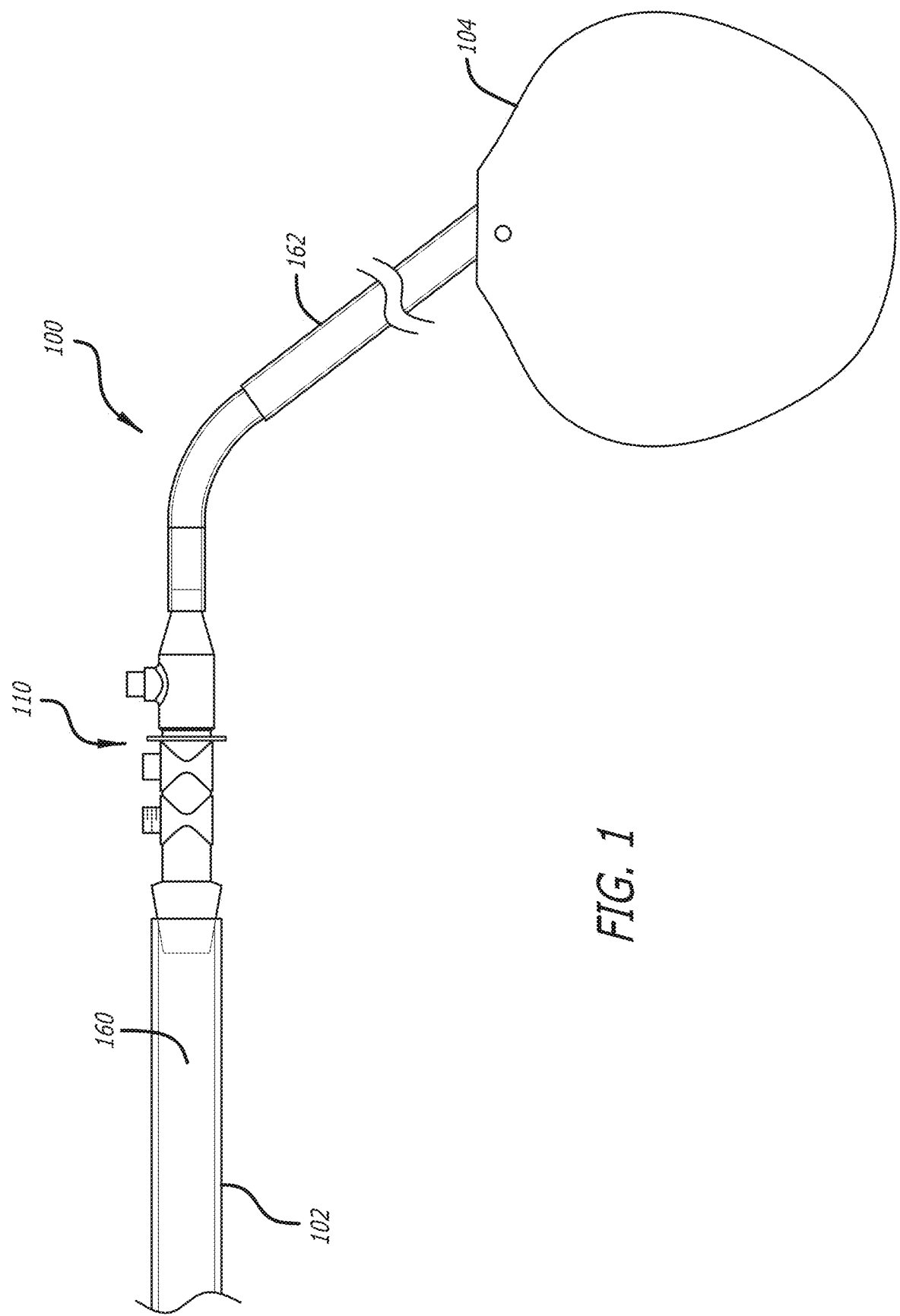
FIG. 1 illustrates a side view of a urinary drainage system including an air pressure apparatus, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, an apparatus disclosed herein includes a portion of the apparatus intended to be near a patient when the apparatus is used on the patient. Likewise, a "proximal length" of, for example, the apparatus includes a length of the apparatus intended to be near or in the patient when the apparatus is used on the patient. A "proximal end" of, for example, the apparatus includes an end of the apparatus intended to be near or in the patient when the apparatus is used on the patient. The proximal portion, the proximal-end portion, or the proximal length of the apparatus can include the proximal end of the apparatus; however, the proximal portion, the proximal-end portion, or the proximal length of the apparatus need not include the proximal end of the apparatus. That is, unless context suggests otherwise, the proximal portion, the proximal-end portion, or the proximal length of the apparatus is not a terminal portion or terminal length of the apparatus.

With respect to "distal," a "distal portion" or a "distal-end portion" of, for example, an apparatus disclosed herein includes a portion of the apparatus intended to be near or in a clinician when the apparatus is used on the patient. Likewise, a "distal length" of, for example, the apparatus includes a length of the apparatus intended to be near clinician when the apparatus is used on the patient. A "distal end" of, for example, the apparatus includes an end of the apparatus intended to be near the clinician when the apparatus is used on the patient. The distal portion, the distal-end portion, or the distal length of the apparatus can include the distal end of the apparatus; however, the distal portion, the distal-end portion, or the distal length of the apparatus need not include the distal end of the apparatus. That is, unless context suggests otherwise, the distal portion, the distal-end portion, or the distal length of the apparatus is not a terminal portion or terminal length of the apparatus.

Unless defined otherwise, all technical and scientific terms used herein have the same meaning as commonly understood by those of ordinary skill in the art.

FIG. 1 illustrates a side view of a urinary drainage system 100 including an air pressure apparatus 110, in accordance with some embodiments. In some embodiments, the urinary drainage system 100 may include a catheter 102 in fluid communication with an air pressure apparatus 110 and a fluid collecting bag 104. In some embodiments, the catheter 102 may be configured to be coupled to the air pressure apparatus 110 by a first drainage tube 160. In some embodiments, the air pressure apparatus 110 may be configured to be coupled to the fluid collecting bag 104 by a second drainage tube 162. In some embodiments, the urinary drainage system 100 may be configured to drain a volume of fluid from a patient and allow fluid flow from the catheter 102 into the fluid collecting bag 104. For example, the catheter 102 may be configured to be inserted into an orifice within the body of a patient to drain body fluid from the catheter 102 to the fluid collecting bag 104. Exemplary catheters include indwelling catheters, Foley catheters, balloon catheters, peritoneal drainage catheters, or the like. Exemplary body fluids can include urine, blood, interstitial fluid, peritoneal fluid, saliva, mucus, or the like.

Figure 2:
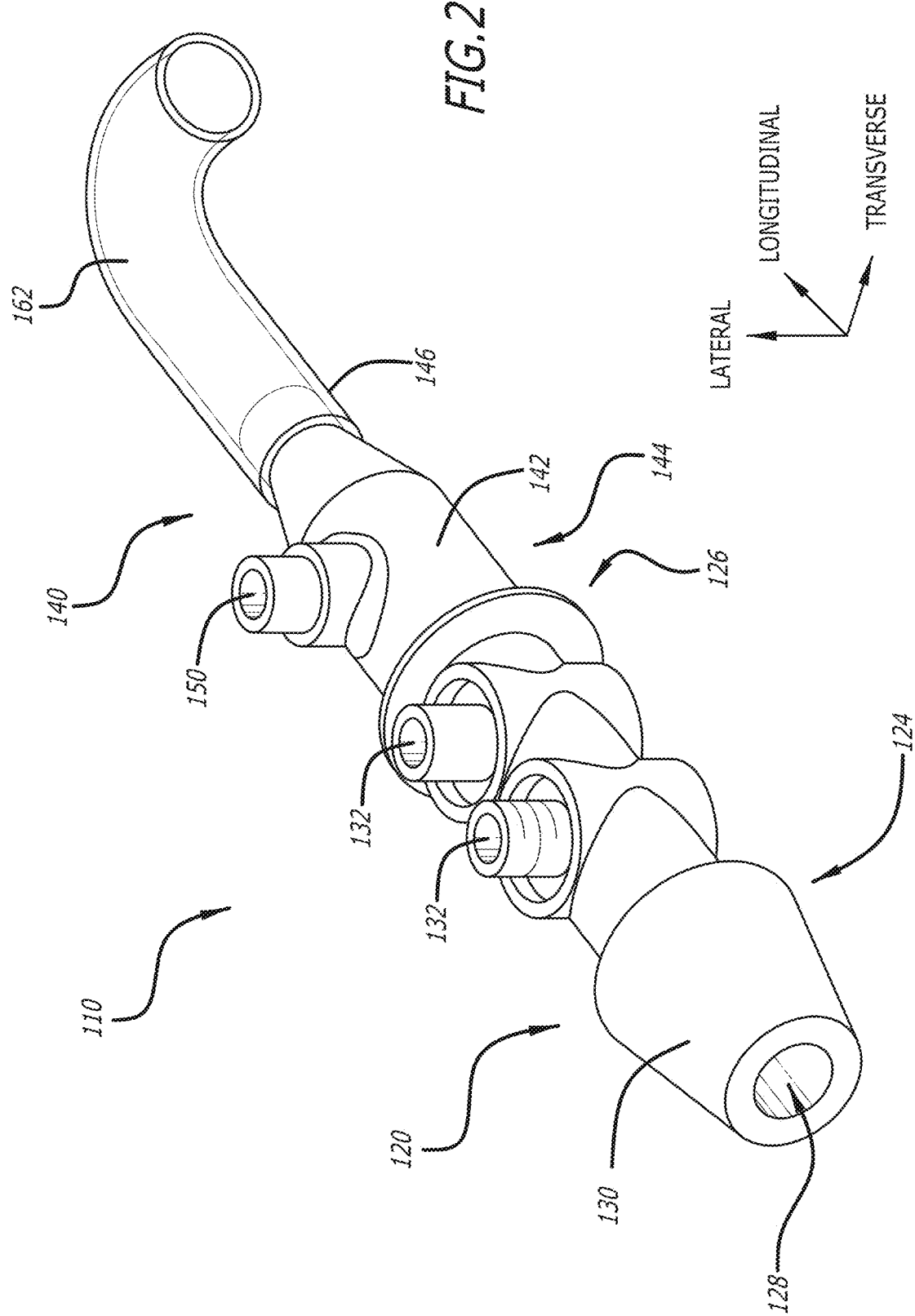
FIG. 2 illustrates a perspective view of the air pressure apparatus, in accordance with some embodiments.

FIG. 2 illustrates a perspective view of the air pressure apparatus 110, in accordance with some embodiments. In some embodiments, the air pressure apparatus 110 includes a connector 120 and an air intake adapter 140 ("adapter") configured to be coupled together. In some embodiments, the air pressure apparatus 110 may be configured to clear a volume of fluid from a drainage tube. In some embodiments, the connector 120 and the adapter 140 may be coupled together in a press fit, a snap fit, an interference fit or the like. In some embodiments, the connector 120 includes a connector body 122, having a proximal end 124, a distal end 126 and a connector lumen 128 therethrough. The connector body 122 may include an elongate body. In some embodiments, the proximal end 124 includes a catheter attachment 130, configured to couple to a catheter 102. In some embodiments, the catheter attachment 130 may be configured to slidably receive a catheter 102 thereon. In some embodiments, the catheter attachment 130 may be configured to slidably receive the first drainage tube 160 thereon.

The adapter 140 includes an adapter body 142, having a proximal end 144, a distal end 146 and an adapter lumen 148 therethrough. In some embodiments, the adapter body 142 may include an elongate body. In some embodiments, the distal end 146 may be configured to couple with the second drainage tube 162. In some embodiments, the distal end 146 may be configured to slidably receive the second drainage tube 162, the second drainage tube 162 in fluid communication with the fluid collection bag. The proximal end 144 of the adapter body 142 may be configured to couple to the distal end 126 of the connector body 122. In some embodiments, the proximal end 144 of the adapter body 142 may be configured to detachably couple to the distal end 126 of the connector body 122. In some embodiments, the proximal end 144 of the adapter body 142 may be configured slidably receive the distal end 126 of the connector body 122. In some embodiments, wherein the connector 120 is slidably engaged by the adapter 140, the connector lumen 128 and the adapter lumen 148 maintain fluid communication between the catheter 102 and the fluid collecting bag 104. In some embodiments, the adapter body 142 may include an air intake port 150 in fluid communication with the adapter lumen 148, that will be described in more detail herein. The air intake port 150 is perpendicular to the adapter lumen 148, advantageously preventing backward airflow into the connector 120 and the first drainage tube 160.

In some embodiments, as illustrated in FIG. 2, the connector body 122 may include one or more lateral ports 132 in fluid communication with the connector lumen 128. The one or more lateral ports 132 may be configured to extend laterally from the connector body 122. The one or more lateral ports 132 may be configured to allow a clinician to withdraw a fluid sample from the connector lumen 128 as a volume of fluid sample passes therethrough. The one or more lateral ports 132 may be configured to be perpendicular to the connector lumen 128. In some embodiments, the one or more lateral ports 132 may be configured to detachably couple with a Luer lock syringe, other medical devices or the like.

Figure 3:
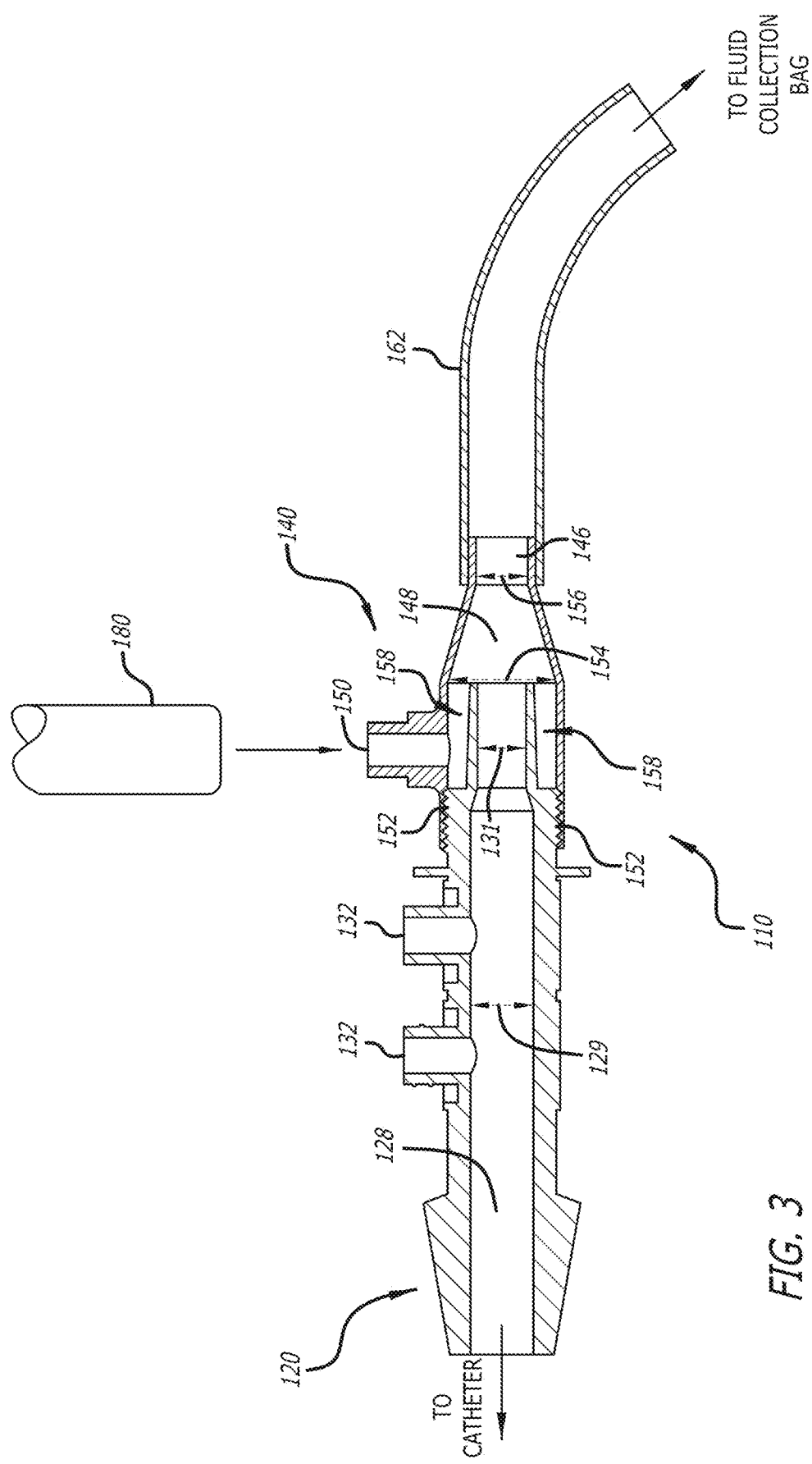
FIG. 3 illustrates a cross sectional view of the air pressure apparatus, in accordance with some embodiments.

FIG. 3 illustrates a cross sectional view of the air pressure apparatus 110, in accordance with some embodiments. In some embodiments, a portion of the distal end 126 of the connector body 122 may include external threads 134 and a portion of the proximal end 144 of the adapter body 142 may include internal threads 152 configured to receive the external threads 134 configured to couple the connector body 122 to the adapter body 142. In some embodiments, the coupling of the distal end 126 of the connector body 122 to the proximal end 144 of the adapter body 142 creates an airtight and fluid seal between the connector body 122 and the adapter body 142, configured to allow a volume of fluid to pass through the connector lumen 128 and the adapter lumen 148.

In some embodiments, the connector lumen 128 has a proximal lumen diameter 129 and a distal lumen diameter 131. In some embodiments, the proximal lumen diameter 129 may be greater than or equal to the distal lumen diameter 131. In some embodiments, the adapter lumen 148 includes a proximal lumen diameter 154 and a distal lumen diameter 156. In some embodiments, the proximal lumen diameter 154 may be greater than or equal to the distal lumen diameter 156. In some embodiments, the proximal lumen diameter 156 of the adapter 140 is greater than the distal lumen diameter 131 of the connector 120. When the connector 120 is coupled to the adapter 140, the difference between the proximal lumen diameter 156 of the adapter 140 and the distal lumen diameter 131 of the connector 120 creates a luminal space 158 within the adaptor body 142, around the distal end 126 of the connector 120. The luminal space 158 is in fluid communication with the air intake port 150 and the adapter lumen 148. In some embodiments, the air intake port 150 may be configured to receive a volume of pressurized air therein and form a vortex of positive pressure air around the distal end 126 of the connector 120 within the luminal space 158, configured to push a volume of fluid from the distal end 126 of the connector 120, through the adapter 140 to the second drainage tube 162. In some embodiments, the proximal lumen diameter 154 and the distal lumen diameter 156 of the adapter 140 may be configured to be increased or decreased to ensure adequate fluid output into the fluid collecting bag 104.

Figure 4:
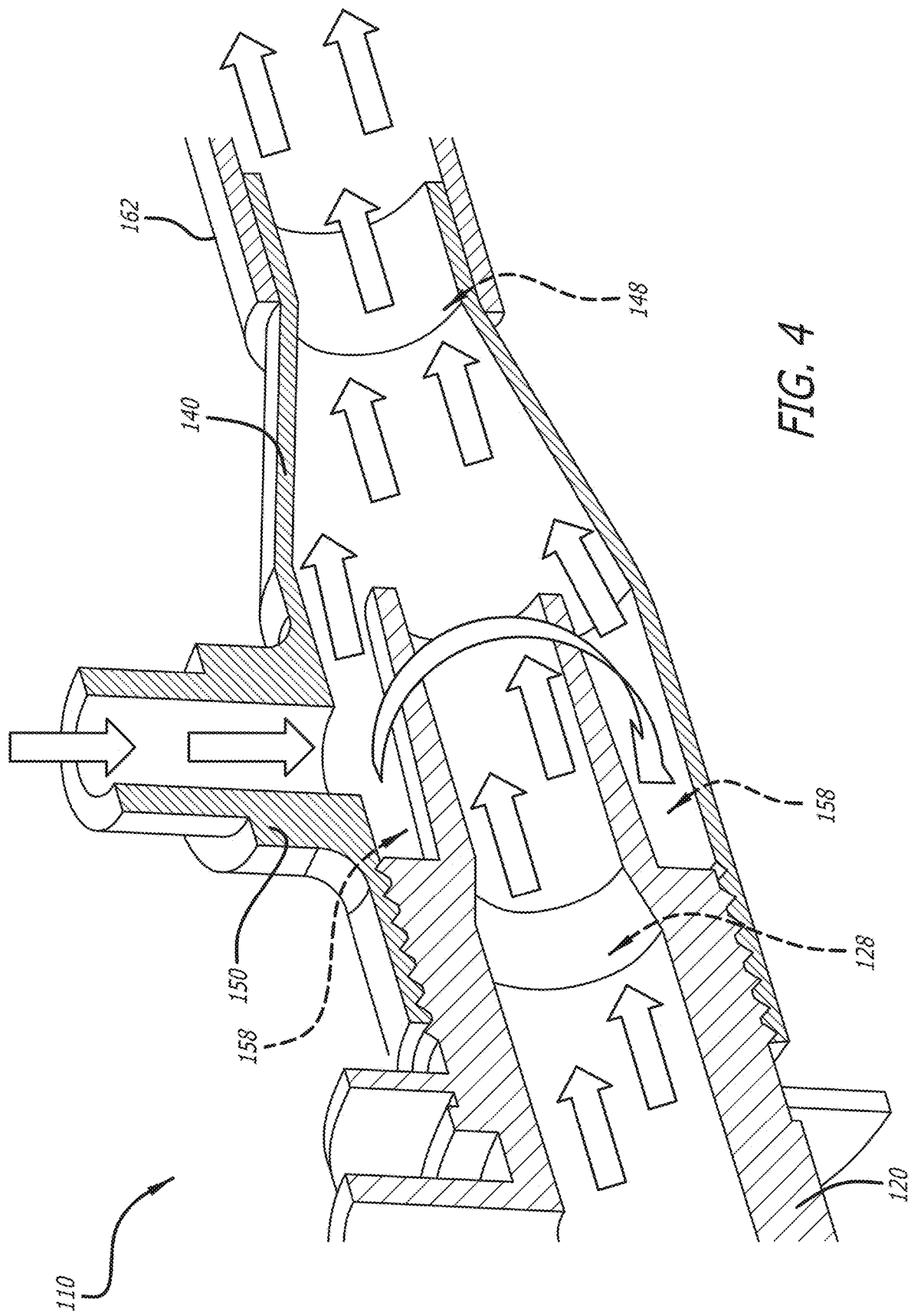
FIG. 4 illustrates an exemplary method of transporting an entirety of a volume of fluid through the air pressure apparatus, in accordance with some embodiments.

FIG. 4 illustrates an exemplary method of transporting an entirety of a volume of fluid through the air pressure apparatus 110, in accordance with some embodiments. In some embodiments, a patient may void a volume of fluid through the catheter 102 in fluid communication with the air pressure apparatus 110 and the fluid collecting bag 104. In some embodiments, the catheter 102 may be in fluid communication with the first drainage tube 160 while the first drainage tube 160 is coupled to the proximal end of the connector 120. The connector 120 is coupled to the adapter 140, maintaining fluid communication between the first drainage tube 160 and the distal end of the adapter 140. The distal end of the adapter 140 is coupled to the second drainage tube 162. An air hose 180, configured to provide the volume of pressurized air through the air intake port 150 may be coupled to the air intake port 150. A volume of fluid may flow from the catheter 102, through the first drainage tube 160, through the connector lumen 128 and the adapter lumen 148 to the fluid collecting bag 104 by gravity flow. It can be appreciated that fluid flow may occur from the catheter 102 to the fluid collecting bag 104 by other mechanisms, all of which are considered. However, a portion of the volume of fluid may remain within the first drainage tube 160. The portion of the volume of fluid remaining within the first drainage tube 160 will be referred herein as the residual volume of fluid.

As illustrated in FIG. 4, to remove the residual volume of fluid remaining within the first drainage tube 160, a volume of pressurized air may be received through the air intake port 150 into the luminal space 158. The volume of pressurized air may be configured to create a positive pressure vortex around the distal end 126 of the connector 120. The positive pressure vortex may be configured to draw the residual volume of fluid from the first drainage tube 160 into the connector lumen 128, through the adapter lumen 148 into the second drainage tube 162. The positive pressure vortex ensures that the entirety of the volume of fluid, including the residual volume of fluid, passes from the distal end 126 of the connector 120, through the adapter 140 to the second drainage tube 162. Advantageously, the positive pressure vortex pushes the residual volume of fluid through the adapter 140 and into the second drainage tube 162, preventing fluid backflow into the first drainage tube 160.

Figure 5:
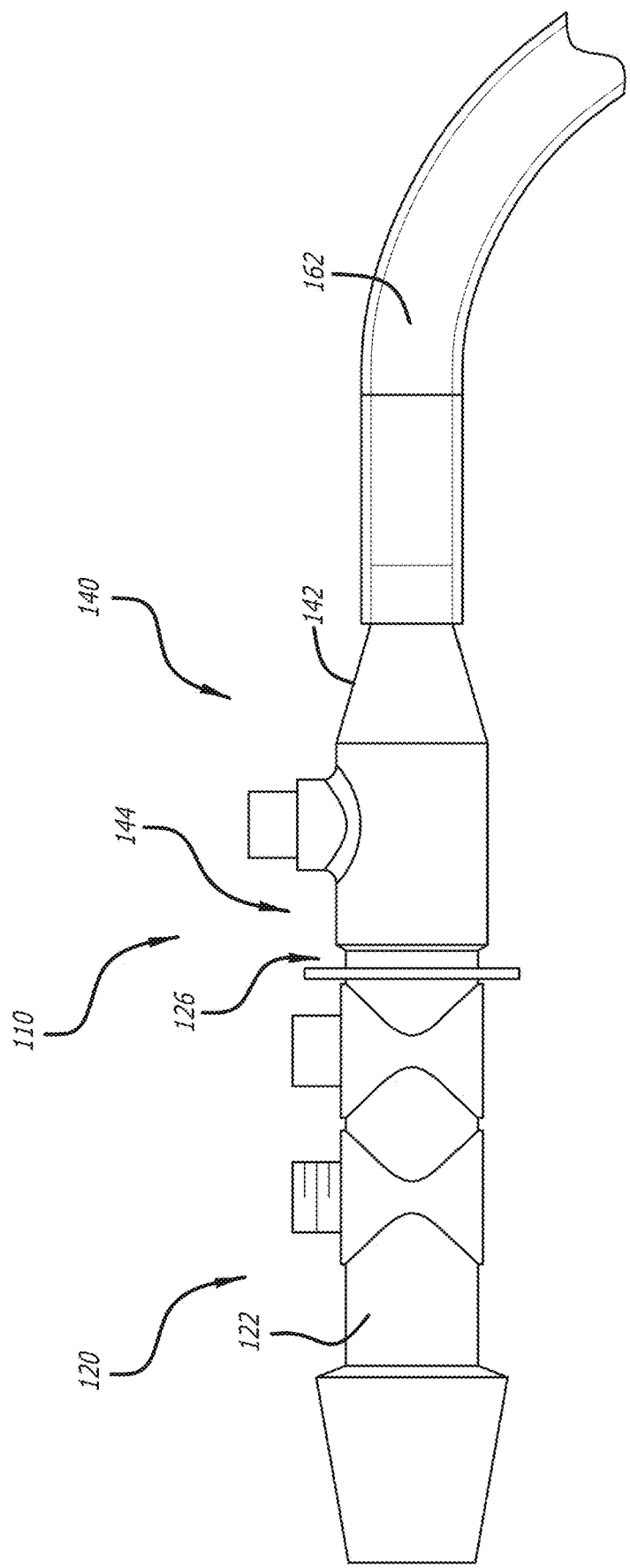
FIG. 5 illustrates a side view of the air pressure apparatus, in accordance with some embodiments.

FIG. 5 illustrates a side view of the air pressure apparatus 110, in accordance with some embodiments. In some embodiments, the connector body 122 and the adapter body 142 may be made from plastic such as polypropylene, polystyrene or the like. In some embodiments, the connector body 122 and adapter body 142 may be injection molded, extruded, 3D printed or the like. In some embodiments, the proximal end 144 of the adapter 140 may be configured to be coupled to the distal end 126 of the connector 120 through snap fit, press fit, interference fit, magnetic fit or the like. In some embodiments, the adapter 140 may be configured to have a locking mechanism configured to lock the connector 120 to the adapter 140 when the proximal end 144 of the adapter 140 slidably receives the distal end 126 of the connecter 120. In some embodiments, the connector 120 and the adapter 140 may be configured to be disposable or reusable.

Figure 6:
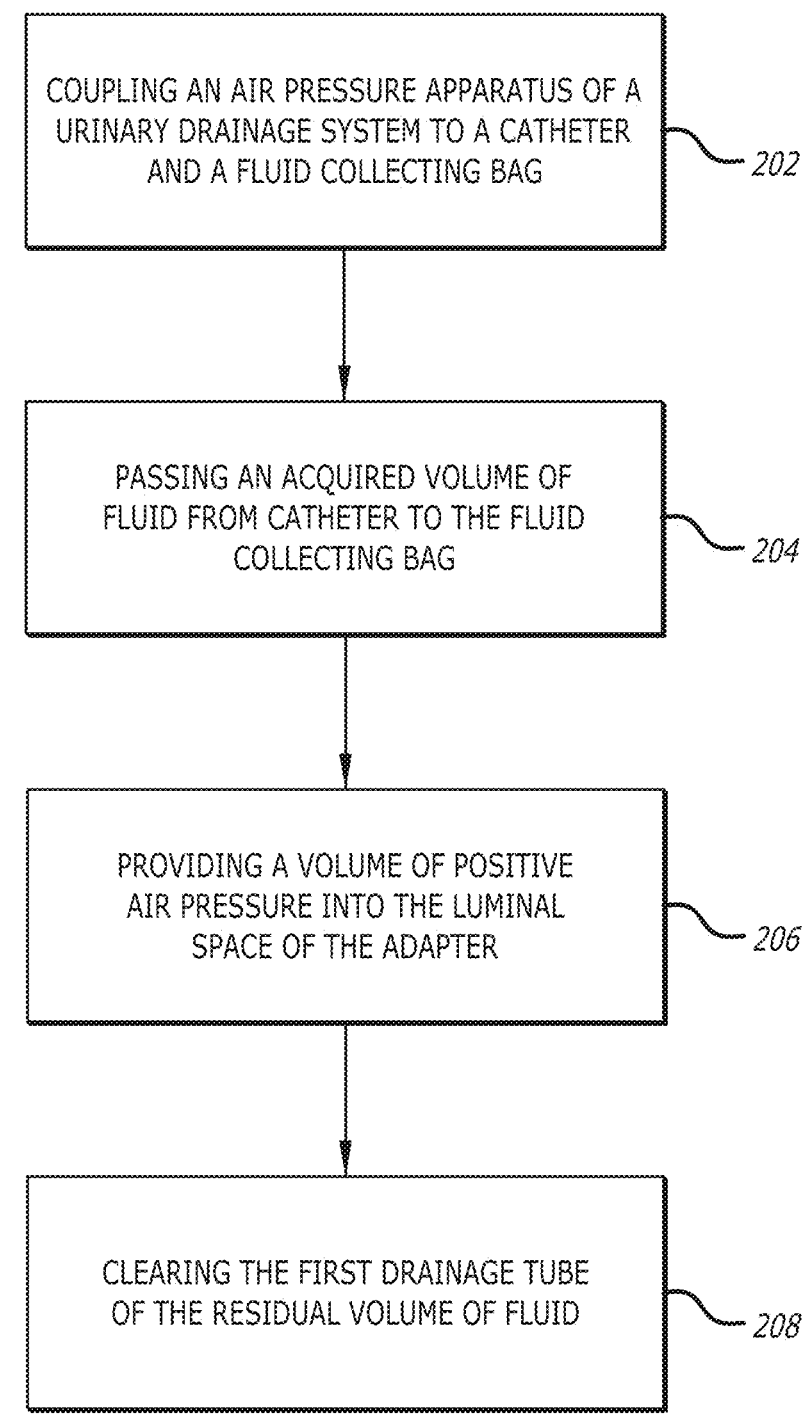
FIG. 6 illustrates a flow chart of an exemplary method of clearing a volume of fluid from a drainage tube, in accordance with some embodiments.

FIG. 6 illustrates a flow chart of an exemplary method of clearing a volume of fluid from a drainage tube, in accordance with some embodiments. The method 200 includes coupling a catheter 102 to the proximal end of an air pressure apparatus 110 of the urinary drainage system 100 and coupling a fluid collecting bag 104 to the distal end of the air pressure apparatus 110 wherein fluid communication occurs between the catheter 102 and the fluid collecting bag 104 (block 202). In some embodiments, the catheter 102 may be coupled to the proximal end of the air pressure apparatus 110 by the first drainage tube 160. In some embodiments, the fluid collecting bag 104 may be coupled to the distal end of the air pressure apparatus 110 by the second drainage tube 162. In some embodiments, the air pressure apparatus 110 includes the connector 120 being coupled to the adapter 140. In some embodiments, the connector 120 includes the connector lumen 128 and the adapter 140 includes the adapter lumen 148 wherein the connector lumen 128 and the adapter lumen 148 are in fluid communication with the catheter 102 and the fluid collecting bag 104. In some embodiments, the adapter 140 may be configured to slidably receive the connector 120 so that the luminal space 158 within the adapter 140 is around the distal end 126 of the connector 120 when the distal end 126 of the connector 120 is received by the adapter 140. In some embodiments, the adapter 140 further includes the air intake port 150 in fluid communication with the luminal space 158, the air intake port 150 configured to receive therein a volume of positive air pressure configured to create the vortex of positive air pressure within the luminal space 158.

The method 200 includes passing an acquired volume of fluid from the catheter 102 to the fluid collecting bag 104 (block 204). In some embodiments, passing includes passing an acquired volume of fluid by gravity flow. The method 200 includes providing a positive volume of air pressure through the air intake port 150 around the luminal space in the adapter (block 206). In some embodiments, providing includes creating a vortex of positive air pressure within the luminal space 158 around the distal end 126 of the connector 120. In some embodiments, providing includes providing the volume of positive air pressure until the entire acquired volume of fluid is contained within the fluid collecting bag 104. The method 200 includes clearing the first drainage tube 162 of the residual volume of fluid (block 208). In some embodiments, clearing includes using the vortex of positive air pressure to draw the residual volume of fluid through the connector lumen 148 and the adapter lumen 128 into the fluid collecting bag 104.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An air pressure apparatus for a urine management system, comprising:
    a connector including a connector lumen along a longitudinal axis; and
    an adapter coupled to the connector forming a fluid tight seal, the adapter comprising:
       an adapter lumen along the longitudinal axis, the connector having a reduced diameter portion extending into the adapter lumen, the reduced diameter portion including an opening in fluid communication with the adapter lumen, wherein a luminal space is defined in the adapter lumen around the reduced diameter portion of the connector, and
       an air intake port including a port lumen orthogonal to the longitudinal axis, the air intake port configured to provide a positive air flow to the luminal space to draw a fluid through the opening of the reduced diameter portion of the connector.

2. The air pressure apparatus according to claim 1, wherein the adapter includes an end downstream of the reduced diameter portion configured to be coupled to a tube.

3. The air pressure apparatus according to claim 2, wherein the tube is in fluid communication with a fluid collection container.

4. The air pressure apparatus according to claim 1, wherein an end of the connector opposite the reduced diameter portion is configured to be coupled to tubing.

5. The air pressure apparatus according to claim 4, wherein the tubing is in fluid communication with a catheter.

6. The air pressure apparatus according to claim 1, wherein the positive air flow to the luminal space is configured to create a vortex around the reduced diameter portion of the connector.

7. The air pressure apparatus according to claim 1, wherein the adapter is coupled to the connector via a threaded engagement.

8. The air pressure apparatus according to claim 1, wherein the adapter is coupled to the connector via a press fit or interference fit engagement.

9. The air pressure apparatus according to claim 1, wherein the connector further comprises one or more lateral ports, each of the one or more lateral ports including a lateral port lumen orthogonal to the longitudinal axis in fluid communication with the connector lumen.

10. The air pressure apparatus according to claim 1, wherein the connector and the adapter are configured to be disposable.

11. A method for an air pressure apparatus, comprising:
    coupling a first end of the air pressure apparatus to a first tube and a second end of the air pressure apparatus to a second tube, the air pressure apparatus comprising:

a connector including a connector lumen along a longitudinal axis; and an adapter coupled to the connector forming a fluid tight seal, the adapter comprising:

an adapter lumen along the longitudinal axis, the connector having a reduced diameter portion extending into the adapter lumen, the reduced diameter portion including an opening in fluid communication with the adapter lumen, wherein a luminal space is defined in the adapter lumen around the reduced diameter portion of the connector; and an air intake port including a port lumen orthogonal to the longitudinal axis;

providing a positive air pressure into the luminal space via the air intake port; and drawing a fluid through the opening of the reduced diameter portion of the connector.

12. The method according to claim 11, wherein providing the positive air pressure includes coupling an air hose connected to a motor to the air intake port of the adapter.

13. The method according to claim 11, wherein providing the positive air pressure includes creating a vortex of positive air pressure around the reduced diameter portion of the connector.

14. The method according to claim 13, wherein drawing the fluid through the opening of the reduced diameter portion of the connector includes using the vortex of positive air pressure to draw fluid from the first tube into the connector lumen.

15. The method according to claim 11, further comprising drawing the fluid from the first tube through the connector lumen and the adapter lumen to the second tube.

16. The method according to claim 15, wherein the second tube is in fluid communication with a fluid collection container.

* * * * *